US008911419B2

(12) United States Patent
Kline et al.

(10) Patent No.: US 8,911,419 B2
(45) Date of Patent: Dec. 16, 2014

(54) ABSORBENT ARTICLE WITH IMPROVED FASTENING SYSTEM (75) Inventors: Mark James Kline, Cincinnati, OH (US); George Christopher Dobrin, Mason, OH (US); Raymond Scott Hamilton, Mason, OH (US); George Bartol Glackin, III, Wyoming, OH (US); Luke Robinson Magee, Cincinnati, OH (US); Miguel Alvaro Robles, Glendale, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 851 days.

(21) Appl. No.: 10/757,629

(22) Filed: Jan. 14, 2004

(65) Prior Publication Data
US 2004/0147899 A1 Jul. 29, 2004

Related U.S. Application Data (63) Continuation of application No. 09/633,422, filed on Aug. 7, 2000, now abandoned.

(51) Int. Cl.
*A61F 13/15* (2006.01)
*A61F 13/62* (2006.01)

(52) U.S. Cl.
CPC .................................... *A61F 13/62* (2013.01)
USPC .................................... 604/386; 604/385.22

(58) Field of Classification Search
USPC ............... 604/358, 398, 399, 394, 386–393; 40/651; 73/827, 841; 112/406; D24/124, 126; 24/578, 522, 610
See application file for complete search history.

(56) References Cited

U.S. PATENT DOCUMENTS

| | | | | |
|---|---|---|---|---|
| 3,708,833 A | * | 1/1973 | Ribich et al. | 24/450 |
| 3,797,495 A | * | 3/1974 | Schmidt | 604/390 |
| 3,937,221 A | * | 2/1976 | Tritsch | 604/390 |
| 4,253,461 A | * | 3/1981 | Strickland et al. | 604/389 |
| 4,846,815 A | * | 7/1989 | Scripps | 604/391 |
| 4,936,840 A | | 6/1990 | Proxmire | |
| 5,019,072 A | * | 5/1991 | Polski | 604/389 |
| 5,151,092 A | | 9/1992 | Buell et al. | |
| 5,312,387 A | * | 5/1994 | Rossini et al. | 604/389 |
| D377,979 S | * | 2/1997 | Plaschko et al. | D24/126 |
| 5,603,708 A | * | 2/1997 | Seth | 604/389 |
| 5,669,897 A | * | 9/1997 | Lavon et al. | 604/385.24 |

(Continued)

FOREIGN PATENT DOCUMENTS

| | | | | |
|---|---|---|---|---|
| CA | 2278867 | | 3/2000 | |
| CA | 2278862 A1 | * | 1/2001 | A61F 13/56 |

(Continued)

*Primary Examiner* — Melanie Hand
(74) *Attorney, Agent, or Firm* — Laura L. Whitmer; Charles R. Ware (57) ABSTRACT The present invention provides an article to be worn about a wearer including a surface fastening system having a primary direction of load bearing. The surface fastening system has a first surface fastening element and a second surface fastening element. The first fastening element is joined to the article, and the second fastening element is disposed so as to be generally in a face to face relationship with the first fastening element when the surface fastening system is in a fastened configuration. The surface fastening system has a peel resistance in a direction other than the primary direction of load bearing greater than or equal to about 1000 grams.

9 Claims, 6 Drawing Sheets

(56) References Cited

U.S. PATENT DOCUMENTS

| | | |
|---|---|---|
| 5,897,545 A | 4/1999 | Kline et al. |
| 5,899,895 A * | 5/1999 | Robles et al. ............ 604/385.29 |
| 5,957,908 A * | 9/1999 | Kline et al. .................. 604/386 |
| 5,984,911 A | 11/1999 | Siebers et al. |
| D422,078 S * | 3/2000 | Vukos et al. ................. D24/126 |
| 6,102,901 A | 8/2000 | Lord et al. |
| 6,942,651 B2 * | 9/2005 | Gibbs .......................... 604/389 |
| 2003/0083635 A1 * | 5/2003 | Gibbs .................... 604/385.04 |
| 2003/0109844 A1 * | 6/2003 | Gibbs .......................... 604/389 |

FOREIGN PATENT DOCUMENTS

| | | |
|---|---|---|
| EP | 0 786 243 A2 | 7/1997 |
| GB | 2 296 179 A | 6/1996 |
| WO | WO 00/35399 | 6/2000 |
| WO | WO 00/37016 | 6/2000 |
| WO | WO 01/43684 A1 | 6/2001 |

\* cited by examiner

ABSORBENT ARTICLE WITH IMPROVED FASTENING SYSTEM

CROSS REFERENCE TO RELATED APPLICATION

This application is a continuation application of prior copending U.S. application Ser. No. 09/633,422 filed on Aug. 7, 2000.

FIELD OF THE INVENTION

The present invention relates to absorbent articles such as diapers, training pants, bibs, sanitary napkins and the like. More specifically, the present invention relates to absorbent articles including improved fastening systems.

BACKGROUND OF THE INVENTION

Absorbent articles and disposable absorbent articles such as diapers, training pants, bibs, sanitary napkins and the like are well known in the art. Such articles are typically used to absorb and contain bodily exudates such as feces, urine and/or menses. Until fairly recently, many of the absorbent articles identified above were made from reusable materials such as woven cloth materials including cotton and other absorbent fabrics. Lately, however, many consumers have found that using disposable absorbent articles is more convenient than using reusable articles for various reasons. Accordingly, many different types of disposable absorbent articles, including disposable diapers such as those described in U.S. Pat. No. 5,151,092 entitled "Absorbent Article With Dynamic Elastic Waist Feature Having Predisposed Flexural Hinge" issued to Buell et al. on Sep. 22, 1992 have achieved wide acceptance and commercial success.

Over the years, there have been many advancements related to disposable absorbent articles, including improvements in fastening systems, absorbency and aesthetics. However, there is still a need for improvement relating to fit, comfort, aesthetics and overall performance of such articles. For example, disposable diapers often do not look or feel like garments. Further, disposable diapers are often difficult for the user, whether it be the caregiver or child, to properly fasten about the wearer. This can lead to poor fit which can result in leaks and/or reduced comfort for the wearer. Further, in diapers for active wearers and in refastenable pull-on diapers, such as described in U.S. Pat. No. 5,987,545 issued to Kline et al., multi-directional resistance to disengagement is important to ensure that the fasteners remain engaged while pulling up the product so that the product does not come apart during application.

One example of an attempt to improve on fastening systems for absorbent articles is disclosed in U.S. Pat. No. 5,984,911 issued to Siebers et al. The patent discloses a fastening system including a foldable trapping panel with a base stationary on the front of the article and a flap panel which extends out from the base. Both the base and the flap include the loop components of a hook and loop fastening device. A complementary hook fastening element is attached to the back of the diaper. Although this system is disclosed to provide improved performance for hook and loop type fastening system, it may not provide the specific performance necessary to function as needed for all product designs, such as for a refastenable pull-on diaper. Further, a fundamental understanding of how such a system works is not disclosed, nor are embodiments that take full advantage of the system.

Accordingly, it would be desirable to provide an absorbent article with an improved fastening system. It would also be desirable to provide an absorbent article with improved aesthetics. It would also be desirable to provide an absorbent article with improved fit and overall performance. Further, it would be desirable to provide an absorbent article with an improved fastening system that provides easier and more reliable fastening performance.

SUMMARY OF THE INVENTION

The present invention provides an article to be worn about a wearer including a surface fastening system having a primary direction of load bearing. The surface fastening system has a first surface fastening element and a second surface fastening element. The first fastening element is joined to the article, and the second fastening element is disposed so as to be generally in a face to face relationship with the first fastening element when the surface fastening system is in a fastened configuration. The surface fastening system has a peel resistance in a direction other than the primary direction of load bearing greater than or equal to about 1000 grams.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

As used herein, the term "absorbent article" refers to devices which absorb and contain body exudates and, more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as absorbent articles (i.e., they are intended to be discarded after a single use and, preferably, to be recycled, composted or otherwise discarded in an environmentally compatible manner). A "unitary" absorbent article refers to absorbent articles which are formed of separate parts united together to form a coordinated entity so that they do not require separate manipulative parts like a separate holder and/or liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, wipes, mops, bandages and the like.

Figure 1:
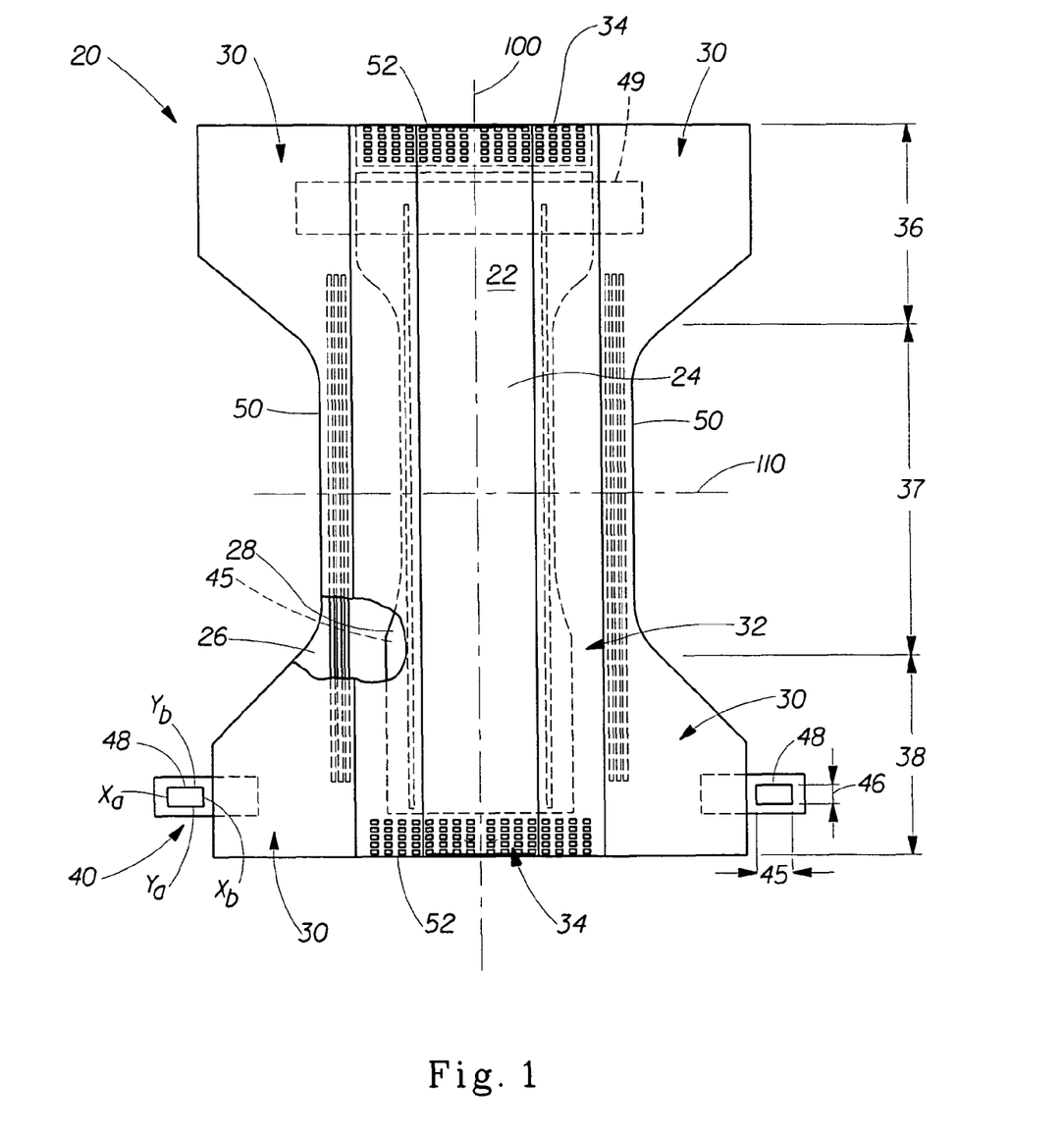
FIG. 1 is a plan view of one embodiment of the present invention in a flat-out, state with portions of the structure being cut-away to more clearly show the construction the article.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28 which is preferably positioned between at least a portion of the topsheet 24 and the backsheet 26; side panels 30; elasticized leg cuffs 32; a waist feature 34; and a fastening system generally designated 40. The diaper 20 is shown in FIG. 1 to have a first waist region 36, a second waist region 38 opposed to the first waist region 36 and a crotch region 37 located between the first waist region 36 and the second waist region 38. The periphery of the diaper 20 is defined by the outer edges of the diaper 20 in which longitudinal edges 50 run generally parallel to the longitudinal centerline 100 of the diaper 20 and end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering including the topsheet 24 and/or the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

The backsheet 26 is generally that portion of the diaper 20 positioned adjacent garment facing surface 45 of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 issued on Aug. 17, 1999 to LaVon et al.; U.S. Pat. No. 5,865,823 issued on Feb. 2, 1999 in the name of Curro; and U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996, and which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. (As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent body surface 47 of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to one or more other elements of the diaper 20.

The topsheet 24 is preferably compliant, soft-feeling, and non-irritating to the wearer's skin. Further, at least a portion of the topsheet 24 is liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the topsheet 24 includes fibers, the fibers may be spunbond, carded, wet-laid, meltblown, hydroentangled, or otherwise processed as is known in the art. One suitable topsheet 24 comprising a web of staple-length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries" issued to Thompson on Dec. 30, 1975; U.S. Pat. No. 4,324,246 entitled "Disposable Absorbent Article Having A Stain Resistant Topsheet" issued to Mullane, et al. on Apr. 13, 1982; U.S. Pat. No. 4,342,314 entitled "Resilient Plastic Web Exhibiting Fiber-Like Properties" issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression" issued to Ahr, et al. on Jul. 31, 1984; and U.S. Pat. No. 5,006,394 "Multilayer Polymeric Film" issued to Baird on Apr. 9, 1991. Other suitable topsheets 30 may be made in accordance with U.S. Pat. Nos. 4,609,518 and 4,629,643 issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, at least a portion of the topsheet 24 is made of a hydrophobic material or is treated to be hydrophobic in order to isolate the wearer's skin from liquids contained in the absorbent core 28. If the topsheet 24 is made of a hydrophobic material, preferably at least a portion of the upper surface of the topsheet 24 is treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and/or immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating a surfactant in the topsheet 24 can be found in U.S. Statutory Invention Registration No. H1670 published on Jul. 1, 1997 in the names of Aziz et al. Each of these references is hereby incorporated by reference herein. Alternatively, the topsheet 24 may include an apertured web or film which is hydrophobic. This may be accomplished by eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" issued to Roe on Mar. 4, 1997; U.S. Pat. No. 5,609,587 entitled "Diaper Having A Lotion Topsheet Comprising A Liquid Polyol Polyester Emollient And An Immobilizing Agent" issued to Roe on Mar. 11, 1997; U.S. Pat. No. 5,635,191 entitled "Diaper Having A Lotioned Topsheet Containing A Polysiloxane Emollient" issued to Roe et al. on Jun. 3, 1997; U.S. Pat. No. 5,643,588 entitled "Diaper Having A Lotioned Topsheet" issued to Roe et al. on Jul. 1, 1997; and U.S. Pat. No. 5,968,025 entitled "Absorbent Article Having a Lotioned Topsheet" issued to Roe et al. on Oct. 19, 1999. The lotion may function alone or in combination with another agent as the hydrophobizing treatment described above. The topsheet 24 may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Exemplary absorbent structures for use as the absorbent core 28 are described in U.S. Pat. No. 4,610,678 entitled "High- Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735 entitled "High Density Absorbent Members Having Lower Density and Lower Basis Weight Acquisition Zones" issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From High Internal Phase Emulsions Having Very High Water-To-Oil Ratios" issued to DesMarais et al. on Jul. 22, 1997. Each of these patents is incorporated herein by reference.

The diaper 20 may also include a sublayer disposed between the topsheet 24 and the backsheet 26. (As used herein, the term "disposed" is used to mean that an element(s) of the diaper is formed (joined and positioned) in a particular place or position as a unitary structure with other elements of the diaper or as a separate element joined to another element of the diaper.) The sublayer may be any material or structure capable of accepting, storing or immobilizing bodily exudates. Thus, the sublayer may include a single material or a number of materials operatively associated with each other. Further, the sublayer may be integral with another element of the diaper 20 or may be one or more separate elements joined directly or indirectly with one or more elements of the diaper 20. Further, the sublayer may include a structure that is separate from the core 28 or may include or be part of at least a portion of the core 28.

Suitable materials for use as the sublayer may include large cell open foams, macroporous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in European Patent Application No. EP 0 847 738 A1 entitled "Disposable Absorbent Article Having Capacity to Store Low-Viscosity Fecal Material" published Jun. 17, 1998 in the name of Roe and U.S. Pat. No. 5,941,864 entitled "Disposable Absorbent Article Having Improved Fecal Storage" issued to Roe on Aug. 24, 199, both of which are hereby incorporated by reference herein. Further, the sublayer, or any portion thereof, may include or be coated with a lotion or other known substances to add, enhance or change the performance or other characteristics of the element.

The diaper 20 may also comprise at least one waist feature 34 that helps to provide improved fit and containment. The waist feature 34 may be elastic and/or extensible, or neither elastic or extensible. If the waist feature 34 is elastic or extensible, it will generally be designed to dynamically fit the wearer's waist. The waist feature 34 preferably extends at least longitudinally outwardly from at least one waist edge of the absorbent core 28 and generally forms at least a portion of the end edge 52 of the diaper 20. Disposable diapers are often constructed so as to have two waist features, one positioned in the first waist region 36 and one positioned in the second waist region 38. Further, while the waist feature 34 or any of its constituent elements may comprise one or more separate elements affixed to the diaper 20, the waist feature 34 may be constructed as an extension of other elements of the diaper 20, such as the backsheet 26, the topsheet 24, or both the backsheet 26 and the topsheet 24.

The waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaperer pulls one elasticized side panel 30 farther than the other during application, the diaper 20 will "self-adjust" during wear.

While the diaper 20 of the present invention preferably has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; and U.S. Pat. No. 6,004,306 entitled "Absorbent Article With Multi-Directional Extensible Side Panels" issued to Robles et al. on Dec. 21, 1999; each of which is incorporated herein by reference.

The diaper 20 preferably further includes leg cuffs 32 which provide improved containment of liquids and other body exudates. Leg cuffs 32 may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs 32 with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper 20, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al. on Dec. 15, 1992 entitled "Disposable Absorbent Article Having Core Spacers"; U.S. Pat. No. 5,397,318 issued to Dreier on Mar. 14, 1995 entitled "Absorbent Article Having A Pocket Cuff"; U.S. Pat. No. 5,540,671 issued to Dreier on Jul. 30, 1996 entitled "Absorbent Article Having A Pocket Cuff With An Apex"; PCT Application WO 93/25172 published Dec. 3, 1993 entitled "Spacers For Use In Hygienic Absorbent Articles And Disposable Absorbent Articles Having Such Spacer"; U.S. Pat. No. 5,306,266 entitled "Flexible Spacers For Use In Disposable Absorbent Articles" issued to Freeland on Apr. 26, 1994; and U.S. Pat. No. 5,997,520 entitled "Disposable Absorbent Article With Selectively Expandable or Inflatable Component" issued to Ahr et al. on Dec. 7, 1999. Examples of compartments or voids are disclosed in U.S. Pat. No. 4,968,312 entitled "Disposable Fecal Compartmenting Diaper" issued to Khan on Nov. 6, 1990; U.S. Pat. No. 4,990,147 entitled "Absorbent Article With Elastic Liner For Waste Material Isolation" issued to Freeland on Feb. 5, 1991; U.S. Pat. No. 5,62,840, entitled "Disposable Diapers" issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets" issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition issued Aug. 5, 1997 to Roe, et al. Examples of other structures especially suitable for management of low viscosity feces are disclosed in U.S. Pat. No. 5,941,864 issued to Roe et al. on Aug. 24, 1999; U.S. Pat. Nos. 5,977,430 issued to Roe et al. on Nov. 2, 1999 and 6,013,063 issued to Roe et al. on Jan. 11, 2000. All of the above-cited references are hereby incorporated by reference herein.

The diaper 20 may also include a fastening system 40. The fastening system 40 preferably maintains the first waist region 36 and the second waist region 38 in a configuration so as to provide lateral tensions about the circumference of the diaper 20 to hold the diaper 20 on the wearer. The fastening system 40 preferably comprises a surface fastener such as tape tabs, hook and loop fastening components and/or hermaphroditic fastening components, although any other known fastening means are generally acceptable. Some exemplary surface fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. An exemplary interlocking fastening system is disclosed in co-pending U.S. application Ser. No. 09/143,184 entitled "Absorbent Article Fastening Device" in the names of Kline et al. filed on Aug. 8, 1998. The fastening system 40 may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 entitled "Disposable Diaper Having An Improved Side Closure" issued to Toussant et al. on Oct. 13, 1987. to reduce shifting of overlapped portions or to improve fit as disclosed in U.S. Pat. No. 5,242,436 entitled "Absorbent Article With Fastening System Providing Dynamic Elasticized Waistband Fit" issued to Weil et al. on Sep. 7, 1993; U.S. Pat. No. 5,499,978 entitled "Absorbent Article With Dynamic Elastic Waist Feature Having A Predisposed Resilient Flexural Hinge" issued to Buell et al. on Mar. 19, 1996; U.S. Pat. No. 5,507,736 entitled "Absorbent Article With Dynamic Elastic Waist Feature Comprising An Expansive Tummy Panel" issued to Clear et al. on Apr. 16, 1996; U.S. Pat. No. 5,591,152 entitled "Absorbent Article With Dynamic Elastic Waist Feature Having A Predisposed Resilient Flexural Hinge" issued to Buell et al. on Jan. 7, 1997. Each of these patents and the co-pending application are incorporated herein by reference. In alternative embodiments, opposing sides of the article may be seamed or welded to form a pant. This allows the article to be used as a pull-on type diaper, such as a training pant.

A surface fastening system 40 is a system in which a fastening element covers or forms at least a portion of the surface of one material and joins that surface to at least a portion of a surface of another material. Examples of surface fastening systems 40 include hook and loop, adhesive, cohesive, hermaphroditic, friction, static and magnetic fasteners. Interlocking fasteners such as buttons, zippers, buckles and the like, however, are not surface fastening systems. A surface fastening system 40 may become disengaged in a peel mode and/or a shear mode. A peel mode exists when one component is held stationary, while the second component is pulled off the first component sequentially by oppositely directed forces acting in a direction including a substantial component of force perpendicular to the surfaces being connected. For example in a hook and loop surface fastening system, each row or line of hooks may be disengaged a little at a time until all the hooks are disengaged from their respective loops. This results in the overall surface fastener being progressively disengaged from a first point to a second point such as from a first edge to a second edge. The peel performance of hook and loop systems is very sensitive to the cost/performance ratio. Generally, to obtain higher peel, a higher basis weight loop must be used which ultimately translates to more loops, thicker fabric, stronger adhesives, and greater overall cost. A shear mode of disengagement, in comparison, exists when the two components are being pulled apart by oppositely directed forces lying in the same plane as the surfaces being joined. The shear mode of disengagement is a sliding, linear action, in contrast to the peel mode disengagement that is a curvilinear type of motion or action. Generally, a surface fastening system requires less force to disengage the system in a peel mode than in a shear mode. Thus, a surface fastening system 40 is more likely to fail in a peel mode than in a shear mode.

In one preferred embodiment of the present invention, a surface fastening system 40 provides for multi-directional resistance to peel mode disengagement. In a refastenable pull-on diaper, for example, the surface fastening system 40 may be subjected to forces in many directions as the diaper is pulled on over the wearer's feet, ankles, knees, buttocks, etc. Thus, it is preferable that the surface fastening system 40 not disengage when it is subjected to these forces. The surface fastening system 40, however, preferably is not difficult to disengage when the diaper is being removed from the wearer. Thus, the surface fastening system 40 preferably has different levels of resistance to disengagement in different directions.

Figure 2:
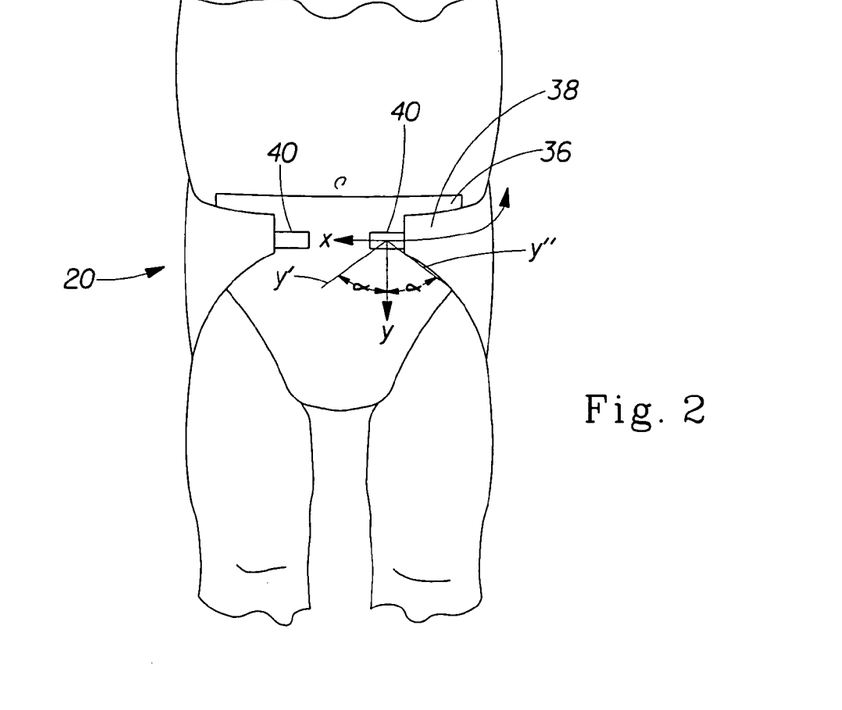
FIG. 2 is a perspective view of one embodiment of the present invention fastened about a wearer.

FIG. 2 depicts a diaper 20 affixed on a wearer. The surface fastening system 40 preferably maintains the first waist region 36 and the second waist region 38 in a configuration so as to provide lateral tensions about the circumference of the diaper 20 to hold the diaper 20 on the wearer. FIG. 2 shows two axes, an x-axis generally oriented about the waist of the wearer and a y-axis generally oriented vertically on the wearer in a standing position. A z-axis is generally perpendicular to the x-axis and the y-axis and extends out of the plane of the figure. In one embodiment, the x-axis defines the primary direction of load bearing (i.e., lateral tensions about the circumference of the diaper around the waist of the wearer hold the diaper on the wearer). In a diaper having a surface fastening system such as a hook and loop, hermaphroditic, adhesive, cohesive and/or magnetic fastener, the diaper is generally removed from the wearer by peeling the edge $X_a$ of the surface fastening system 40 away in the xz-plane such that the surface fastening system 40 is progressively disengaged by peeling from the distal edge $X_a$ to the proximal edge $X_b$ along the x-axis. Thus, the surface fastening system 40 preferably is not difficult to peel in the xz-plane from the distal edge $X_a$ to the proximal edge $X_b$ so that the diaper may be easily removed from the wearer. Alternatively, at least a portion of the distal edge $X_a$ is preferably easier to remove in order to start the peeling action. Thus, it is preferable that at least a portion of the distal edge $X_a$ of the surface fastening system is not difficult to disengage in a peel mode by a force located substantially in the xz-plane for at least a portion of the path from the distal edge $X_a$ to the proximal edge $X_b$, however, the surface fastening system may become progressively more difficult to disengage as the peel mode disengagement progresses toward the proximal edge $X_b$. When the wearer is active or when a diaper is pulled onto the wearer, the surface fastening system 40 will also preferably remain fastened in the presence of peel forces in directions other than in the xz-plane that are greater than the peel force that will disengage at least a portion of the surface fastening system 40 in the xz-plane. The surface fastening system 40 includes longitudinally inboard edge $Y_a$ and longitudinally outboard edge $Y_b$. Further, FIG. 2 depicts axes y' and y" that are offset from the y-axis by an angle □ on either side of the y-axis.

Preferably, the surface fastening system 40 is able to remain fastened when subjected to peel forces in all the planes between the y'z-plane and the y"z-plane, including the yz-plane when the peel forces act on the longitudinally inboard edge $Y_a$ and/or the longitudinally outboard edge $Y_b$. Preferably, the surface fastening system 40 is able to remain fastened when subjected to peel forces in a direction other than in the xz-plane, most preferably including the y'z-plane through the y"z-plane, that are greater than about 1000 grams, more preferably greater than about 1300 grams, even more preferably greater than about 1600 grams, and yet even more preferably greater than about 2000 grams. The angle □ is preferably about 20 degrees, more preferably about 30 degrees, even more preferably about 40 degrees, yet even more preferably about 50 degrees and most preferably about 60 degrees. Preferably, however, at least a portion of the distal edge $X_a$ of the surface fastening system 40 may become disengaged in a peel mode by a force oriented in the xz-plane that is less than the force that will cause the surface fastening system 40 to become disengaged in a peel mode by a force in a direction other than in the xz-plane, more preferably at least a portion of the distal edge $X_a$ of the surface fastening system 40 may become disengaged in a peel mode by a force directed in the xz-plane less than or equal to about 1000 grams, even more preferably at least a portion of the distal edge $X_a$ of the surface fastening system may become disengaged in a peel mode by a force directed in the xz-plane less than or equal to about 750 grams, yet even more preferably at least a portion of the distal edge $X_a$ of the surface fastening system may become disengaged in a peel mode by a force directed in the xz-plane less than or equal to about 500 grams.

A surface fastening system 40 of the present invention may be designed to achieve a certain resistance to peel mode disengagement of a surface fastener. For example, changes in design, structure, attachment and/or material may affect the resistance of the surface fastening system 40 to peel mode disengagement. A change in design may include the dimension of the fastener at the edge that is resisting peel mode disengagement or the overall shape of the engaging area. A longer edge length for the fastener results in a greater resistance to peel mode disengagement along that edge. For example, a surface fastener having a resistance to peel mode disengagement of about 800 grams along a 0.5 inch edge will generally have a resistance to peel mode disengagement of up to about 1600 grams at the edge if the length of the edge is increased to about one inch. Also, the overall shape of the engaging area of the surface fastening system 40 may be optimized to minimize the cost and/or difficulty in disengaging the surface fastening system 40 in one direction while maximizing the resistance to peel mode disengagement in another direction. On some fasteners, the resistance to peel mode disengagement in various directions may also be selectively enhanced or reduced by enhancing or damaging portions of the fasteners. Further, the structure may be modified in order to increase or decrease the resistance of the fastener to peel mode disengagement such as by including a flap or a hinge 44 that protects the edge of the fastener from disengaging in a peel mode, by attaching all or a portion of the edge to the underlying structure of the diaper 20 or by leaving the edge unattached to the underlying structure of the diaper 20. The resistance to peel mode disengagement may also be affected by the selection of the fastening materials used in the surface fastening system 40. For example, some fastening materials have an inherently higher resistance to peel mode disengagement than other materials, commonly referred to as an aggressive fastener. Although use of an aggressive fastening material may increase the resistance to peel mode disengagement in the desired direction, the use of this material, in the absence of other design criteria, may result in an unacceptably high resistance to peel mode disengagement in another direction. In certain preferred embodiments, the fastening system may have inherent directionality in peel resistance thus enabling peel to be maximized in one or more directions with minimal or no increase in peel in other directions. For example, hooks may be manufactured having an orientation as disclosed in U.S. Pat. No. 6,054,091 issued to Miller, et al on Apr. 25, 2000 and U.S. Pat. No. 5,325,415 issued to Goulait, et al on Jul. 5, 1994, each of which is incorporated by reference. In such hooks or other fastening materials with inherent directionality, the orientation inherent in the raw material may not result in the desired orientation in the product. In such cases, the fastening material may be re-oriented during manufacture of the product in order to result in the desired directionality on the finished product.

Exemplary Embodiments

Examples of fastening systems 40 of the present invention are described in detail below. These examples are meant to describe several systems that meet the functional requirements of the present invention and are non-limiting. One skilled in the art may be able to build different examples based upon the concepts taught in this detailed description in order to achieve the desired functional characteristics of the present invention.

Figure 3:
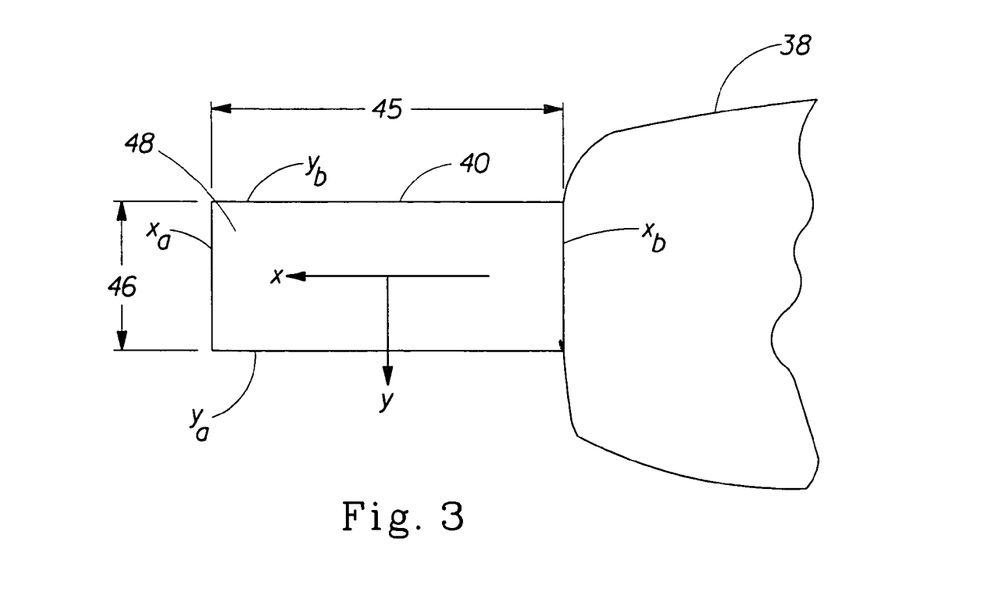
FIG. 3 is an expanded view of a portion of the fastening system shown in FIG. 2.

FIG. 3 shows one example of a design in which the dimensions of the engaged area of the fastening element(s) are optimized for a higher resistance to peel mode disengagement in the yz-plane and a lower resistance to peel mode disengagement in the xz-plane. In FIG. 3, the fastening material includes two dimensions, an x-direction 45 generally oriented along the x-axis as shown in FIG. 2, and a y-direction 46 generally oriented along the y-axis shown in FIG. 2. In this embodiment, the horizontal or x-direction dimension is longer than the vertical or y-direction dimension. Thus, the resistance to peel mode disengagement may be greater in the yz-plane than in the xz-plane. In one particular embodiment, for example, the surface fastening system 40 may include a hook and loop fastener in which at least the engaged area in common between the hook fastening element and the loop fastening element have the shape as shown in FIG. 3 when configured as intended for use of the article. The hook fastening element, for example, may have an x-dimension 45 of about 1.0 inch and a y-dimension 46 of about 0.5 inch. The loop fastening element may have the same or larger dimensions as the hook material. In this embodiment, the resistance to peel mode disengagement in the yz-plane may be about twice that of the resistance to peel mode disengagement in the xz-plane for hook and loop systems with minimal inherent directionality. Alternatively in this example, the resistance to peel mode disengagement in the yz-plane may be greater than twice the resistance to peel mode disengagement in the xz-plane if the hook and loop system has high inherent directionality with peel maximized for the yz-plane direction. Alternatively, the surface fastening system 40 may include an adhesive fastener in which at least one of the adhesive tape element and the landing zone (also known as the receiving surface for an adhesive tape system) element have the shape as shown in FIG. 3. By altering the x-dimension 45 relative to the y-dimension 46, preferred ranges of yz-plane peel resistance and xz-plane peel resistance can be acheived.

Figure 4A:
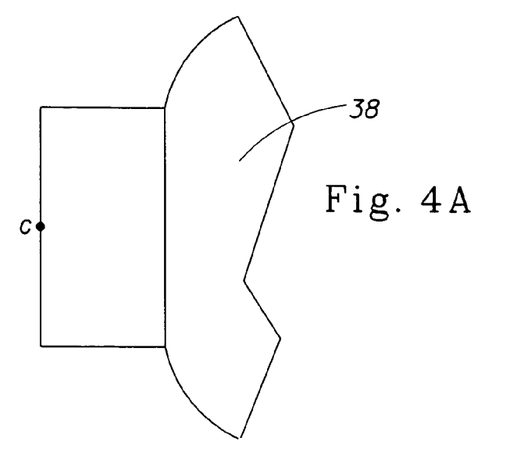
FIGS. 4A through 4C are plan views of alternative embodiments of a fastening system of the present invention.
Figure 4B:
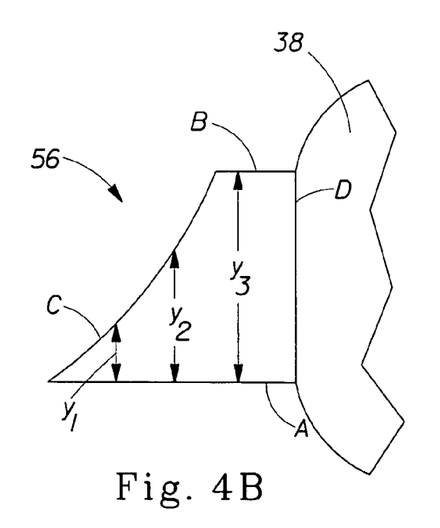
Figure 4C:
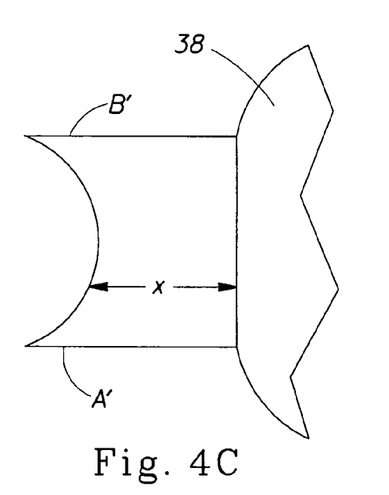

In another embodiment, the shape of the engaged area of the fastening element(s) may be optimized for a higher resistance to peel mode disengagement in the yz-plane and a lower resistance to peel mode disengagement in the xz-plane. FIGS. 4A through 4C, for example, show possible shapes of fastening elements that may be used in a fastening system. FIG. 4A shows a typical rectangular-shaped fastening element. FIG. 4B shows one embodiment of a fastening element of the present invention in which the shape of the engaged area of the fastening element has been designed in order to decrease the resistance to peel mode disengagement in the yz-plane as peel progresses from edge A to edge B by decreasing the effective x-dimension along at least a portion of the path from edge A to edge B. Thus, the resistance to yz-plane peel is initially higher at edge A and may decrease at some point between edge A and edge B. The initial peel resistance at the laterally inboard edge C, however, has been decreased by shaping the laterally inboard edge C so that the effective dimension in the y-direction increases for at least a portion of the path from edge C to laterally outboard edge D. For example, as shown in FIG. 4B, y-dimension Y1 is smaller than Y2 and Y3. Thus resistance to peel in the xz-plane is initially lower at edge C, then may increase along the path to edge D. In one particular embodiment, the surface fastening system 40 may include a hook and loop fastener in which at least the engaged area in common between the hook element and the loop element are shaped as the fastening element 56 shown in FIG. 4B when configured as intended for use of the article. That is, in general, the effective length of dimension Y increases along at least a portion of the path from edge C to edge D, and the effective dimension X decreases along at least a portion of the path from edge A to edge B. In certain embodiments such as shown in FIG. 4C, the effective dimension X may initially decrease or increase along a portion of the path from edge A' to edge B' then increase or decrease along another portion of the path from edge A' to edge B'.

Figure 5:
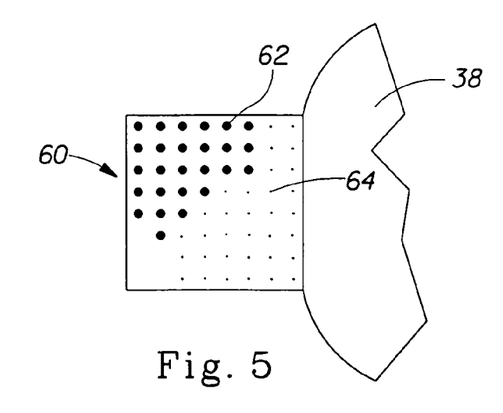
FIG. 5 is plan view of an alternative embodiment of a fastening system of the present invention.

In alternative embodiments, the peel resistance of a surface fastening system 40 may be selectively altered by varying the effective shape of the engaged area of the surface fastening system 40 in addition or as an alternative to altering the actual shape of the engaged area of surface fastening system 40 as discussed above. For example, FIG. 5 shows yet another particular embodiment of a surface fastening system 40 of the present invention in which a generally rectangular patch of fastening material is rendered effectively trapezoidal shaped by selectively damaging a portion of one or more of the fastening elements. For example, portions of the fastening element 60 may be damaged such as by mechanical bonding, ultrasonic bonding, selective heating, or any other process capable of selectively or otherwise disabling a portion of a fastening element. In this embodiment, a first portion 62 of the fastening element 60 may be selectively damaged in order to lower the peel resistance of the surface fastening system 40 in that area, and a second portion 64 may be used to provide a higher peel resistance in an area where the higher peel resistance is desired.

Figure 6:
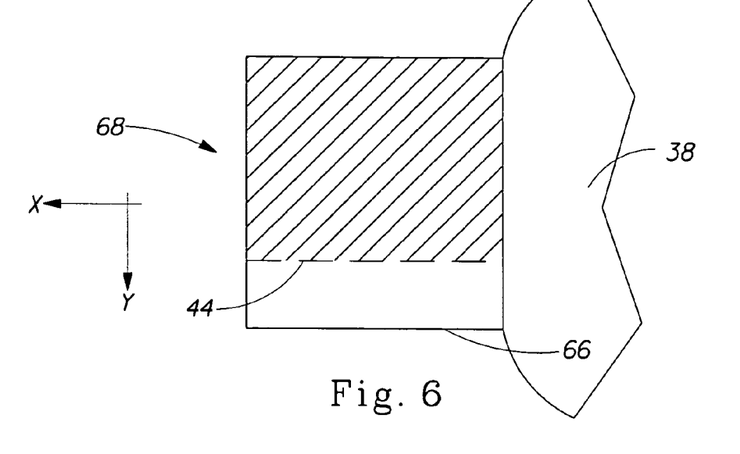
FIG. 6 is a plan view of an alternative embodiment of a fastening system of the present invention.
Figure 7:
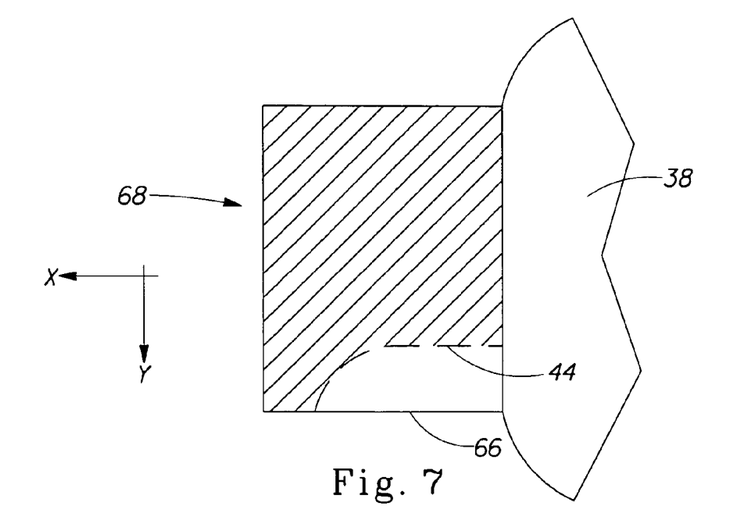
FIG. 7 is a plan view of an alternative embodiment of a fastening system of the present invention.
Figure 8:
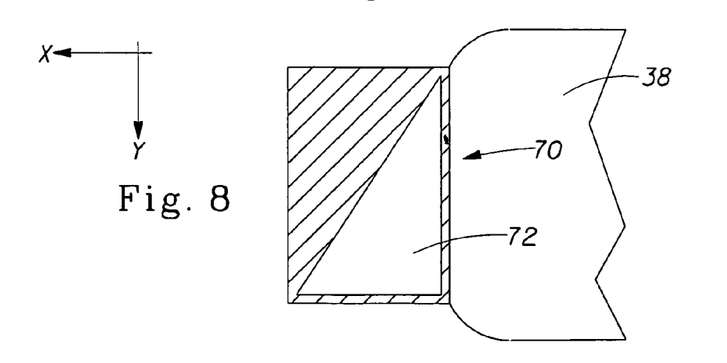
FIG. 8 is a plan view of an alternative embodiment of a fastening system of the present invention.

FIGS. 6, 7 and 8 show embodiments in which the peel resistance of the surface fastening system 40 may be selectively enhanced. In FIGS. 6 and 7, for example, all or a portion of edge 66 of fastening element 68 may be unjoined from the underlying structure of the article 20. In these figures, the portion of the fastening element 68 joined to the underlying structure of the article 20 is shown cross-hatched. In this embodiment, all or a portion of the edge 66 of the fastening element 68 is free to pull away from the underlying structure of the article 20. This may increase the peel resistance of the surface fastening system 40. Without being bound by theory, it is believed that as the edge pulls away from the underlying structure of the article 20, the disengagement mode shifts gradually away from a peel mode to a shear mode of disengagement. In many surface fasteners such as a hook and loop fastener, it is more difficult to disengage the fastener in shear mode than in peel mode. Thus, the resistance to disengagement of the fastener to a force in the yz-plane may be increased. In another embodiment, such as shown in FIG. 8, a portion 72 of the fastening element 70 other than the edge may be unjoined from the underlying structure of the article 20. In this fastener, the peel resistance in this portion 72 of the fastener may be selectively increased. In addition, in embodiments in which at least a portion of fastening element 68 is joined to a carrier web and at least a portion of the carrier web and/or fastening element 68 may be unjoined from the underlying structure of the article 20, at least a portion of the carrier web or the fastening element 68 can be extensible or elastomeric. For example, a vacuum formed elastomer material such as described in U.S. patent application Ser. No. 08/816,106 filed on Mar. 14, 1997, which is incorporated by reference, may be used. Any other extensible and/or elastomeric/elastic materials, including those previously referenced herein, may also be used. Embodiments have also been contemplated in which at least a portion of fastening element 68 is joined to a carrier web, and at least a portion of the carrier web and/or fastening element 68 may be unjoined from the underlying structure of the article 20 and at least a portion of the carrier web is extensible or elastomeric.

The above described approaches may be used alone or in combination to achieve the desired peel resistance in the yz- and xz-planes. Thus, by changes in design, structure, attachment and/or material, a system may be created to meet the functional requirements defined herein for resistance of the surface fastening system 40 to peel mode disengagement.

In other preferred embodiments, the product may be delivered to the consumer at least partially pre-fastened. For example, fastening elements 48 of the fastening system 40 may be joined with a second fastening element(s), such as landing zone fastening elements 49, during the article's manufacture in order to pre-fasten the fastening system 40. Pre-fastening of the product during its manufacture allows the consumer to slip the product over the wearer's feet and pull it in place about the torso as one does a traditional pull on article. Yet, the fasteners enable the user to disengage the fasteners if they so choose and fasten the article about the wearer without needing to remove lower body clothing, such as pants, stockings, or shoes.

Figure 9:
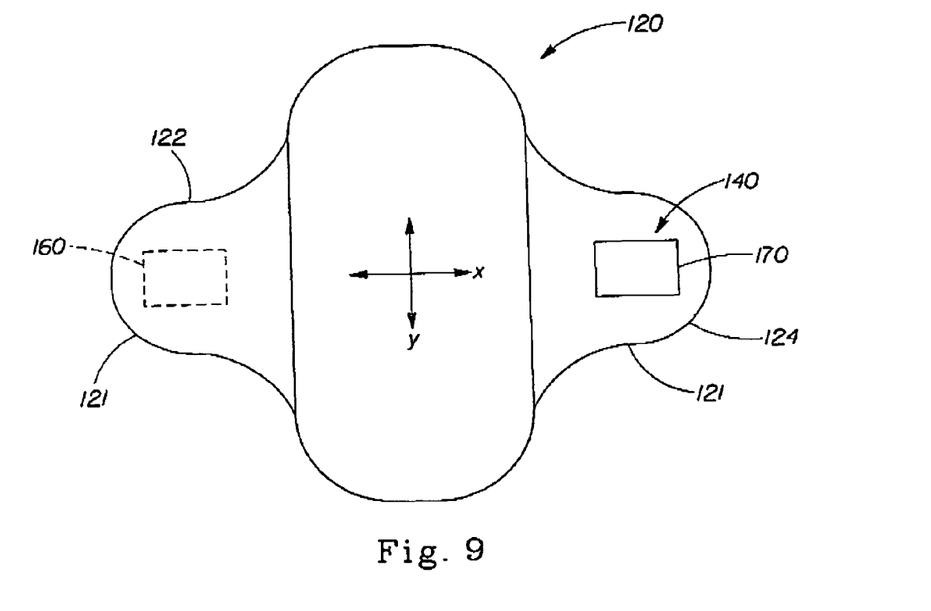
FIG. 9 is a plan view of a sanitary napkin including an alternative embodiment of a fastening system of the present invention.

FIG. 9 shows an example of an alternative embodiment of the present invention such as a sanitary napkin or light incontinent pad that includes the fastening system 140 of the present invention to hold the sanitary napkin or light incontinent pad in a configuration wrapped around a wearer's panties or underwear. For example, the fastening system 140 may be used to fasten wings 121 of a sanitary napkin 120 about a wearer's panties. Fastening the wings 121 of a sanitary napkin about the wearer's undergarment may help ensure that the sanitary napkin 120 will stay in place while in use and provides a means for reducing the likelihood that the undergarment will be soiled if the core of the sanitary napkin 120 should leak. The fastening system 140 of the sanitary napkin 120, for example, may include a first fastening element 160 and a second fastening element 170. As shown in FIG. 9, for example, the first fastening element 160 may be located on the first wing 122 and the second fastening element 170 may be located on the second wing 124. The wings 121 extend outwardly from the longitudinal edges 150 of the sanitary napkin 120. Alternatively, the first fastening element 160 or the second fastening element 170 may be disposed on a portion of the backsheet 126 of the sanitary napkin 120 in a configuration similar to any of the embodiments described above with respect to a diaper. As described above with respect to other embodiments of the present invention, the fastening elements 160 and 170 may comprise any known surface fastening means, such as hooks, loops, adhesive, cohesive, magnets, and the like or any combination of any of these fasteners. The first fastening element 160 and/or the second fastening element 170 may also include any of the embodiments described above with respect to the fastening systems shown in FIGS. 1 through 8. Although the fastening system 140 is shown in FIG. 20 as the primary fastening device, the surface fastening system 140 of the present invention may be used in conjunction with other means for securing the napkin to the undergarment or around the undergarment such as adhesives, cohesives, hooks, loops, friction, static, magnets, and/or any other means known in the art. The surface fastening system 140 may also be used to fasten the sanitary napkin 120 to other devices such as belts or other sanitary guards, or may be used as a means for wrapping the sanitary napkin 120 in a disposal configuration. Examples of sanitary napkins with which the fastening system 140 of the present invention may be used are described in detail in U.S. Pat. No. 5,267,992 entitled "Shaped Sanitary Napkin With Flaps" issued to Van Tilburg on Dec. 7, 1993, and U.S. Pat. No. 5,389,094 entitled "Absorbent Article Having Flaps and Zones of Differential Extensibility" issued to Lavash et al. on Feb. 14, 1995, each of which is incorporated by reference herein.

Figure 11:
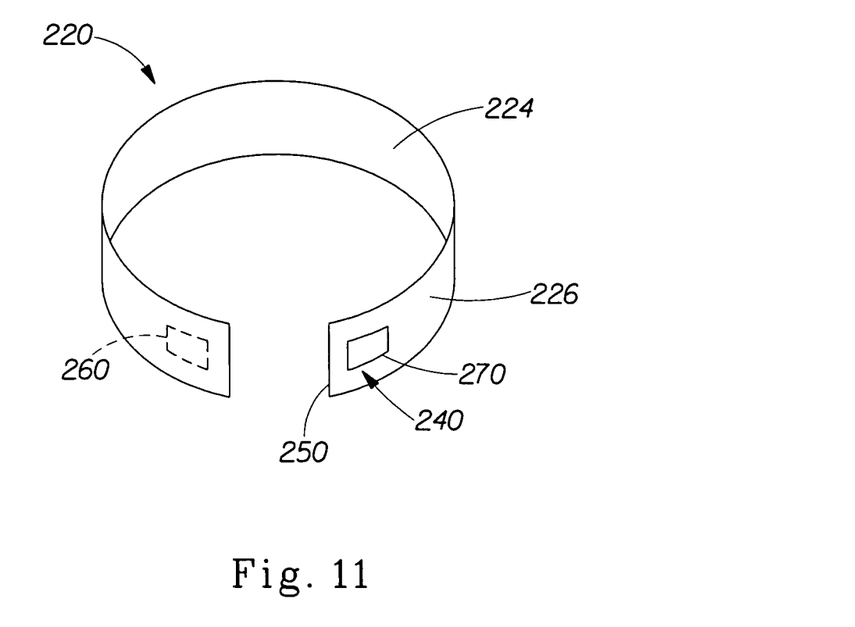
FIG. 11 is an plan view of a body wrap including an alternative embodiment of a fastening system of the present invention.

In yet another embodiment, a body wrap may include a fastening system 240 of the present invention to hold the body wrap in a fastened configuration around a portion of a wearer's body such as around the wearer's waist, torso, leg, ankle, foot, arm, wrist, hand, neck, head, etc. FIG. 11, for example, shows one possible embodiment of a body wrap 220 of the present invention having a fastening system 240 including a first fastening element 260 and a second fastening element 270. The first fastening element 260 and the second fastening element 270 may extend outwardly from an end edge 250 of the body wrap 220. Alternatively, the first fastening element 260 and/or the second fastening element 270 may be disposed on a portion of the an inner surface 224 or an outer surface 226 of the body wrap 220. Further, the first and/or second fastening elements 260 and 270 may be configured in a configuration similar to any of the embodiments described above with respect to a diaper or sanitary napkin and/or shown in FIGS. 1 through 9. One or more of the first fastening element 260 or the second fastening element 270 may include one or more surface fastening elements disposed on one or more surface of the body wrap 220, and the fastening elements 260 and 270 may comprise any known surface fastening means, such as those described above. Further, the fastening elements 260 and/or 270 may also include any of the embodiments described above with respect to the fasteners shown in FIGS. 1 through 9. Examples of body wraps with which the surface fastening system 140 of the present invention may be used are described in detail in U.S. Pat. No. 5,741,318 entitled "Elastic Back Wrap Having Diamond-Shaped Thermal Pattern and Anti-slip Means" issued to Oullette et al. on Apr. 21, 1998, and U.S. Pat. No. 5,860,945 entitled "Disposable Elastic Thermal Knee Wrap" issued to Cramer et al. on Jan. 19, 1999, each of which is incorporated by reference herein.

Test Methods

T-Peel Strength Method

The peel mode disengagement force is determined according to the method described below, which is an adaptation of ASTM Designation D5170-91, "Standard Test Method for Peel strength ("T" method) of hook and loop touch fasteners" Other references relevant to running the peel mode disengagement force test using tensile testing machines include ASTM Designation D 76, "Specifications for Tensile testing Machines for Textiles," and ASTM Designation E 4, "Standard Practice for verification of Testing Machines." This method is intended for determining the relative peel resistance of a surface fastening system by means of a T-type specimen. T-Peel is the load to produce progressive separation of two bonded, flexible adherends.

Apparatus

The following apparatuses are used: a Constant rate of extension Tensile Tester, Jaws, Scissors, a Load Cell and an eleven pound (11 lb.) hand operated roller. The Constant rate of extension Tensile Tester is a universal constant rate of extension tensile testing machine that complies with the requirements of ASTM D76. The Jaws include two clamps with centers in the same plane, parallel to the direction of the motion of the stressing clamp, and so aligned that they will hold the specimen ends wholly in the same plane. The faces must be wide enough to include the entire specimen. In the test, a load cell is selected so that the tensile results for the strip tested will be between 20% and 80% of the load range used. The load cell preferably meets the specification of ASTM Designation E-4. The eleven pound (11 lb.) hand operated roller is a steel roller measuring 82.6 mm (3.35 inch) ☐ 2.5 mm (0.1 inches) diameter, 44.4 mm (1.75 inch) ☐ 1.3 mm (0.05 inches) in width, covered with rubber approximately 6.4 mm (0.25 inches) in thickness and having Shore scale A durometer hardness of 80 ☐ 5. The surface of the roller shall be a true cylinder void of any concave or convex deviations. The mass of the roller is 11 lbs. ☐ 0.1 lb.

Facilities

For the purposes of this test method, a conditioned room refers to a room controlled to 23.0° ☐ 1.0° C. (73.4° ☐ 1.8° F.) and 50% ☐ 2% relative humidity.

Preparation and Calibration of Instruments

The instruments are prepared and calibrated by the following steps:
  (1) Calibrate the tensile tester according to manufacturer's instructions. Choose a Load Cell so that tensile results for the strip tested will be between 20% and 80% of the load range used.
  (2) Set the gage length to 38 mm (1.5 inches).
  (3) Set the instrument crosshead to operate at 254 mm/minute (10.0 inches/minute).
  (4) If the tensile tester is computer interfaced, set the program to mark the Peak Load.

Sample Preparation

The sample to be tested is prepared according to the following steps:
  (1) Condition samples a minimum of two hours prior to testing, according to conditions stated in the facilities section of this method.
  (2) Attach a first leader to the first fastener portion. The leader should extend about 3 inches from the edge of the fastener and be about the same width as the widest portion of the fastening system. The leader should be an extension of the material on which the fastener is mounted on the product. If this is not possible, a suitable material should be chosen with similar modulus and bending stiffness as the material on which the fastener is mounted on the article. If the fastening system is not joined directly to the underlying structure of the article, as shown in FIGS. 6, 7, and 8 and described herein, the leader should be joined to the underlying structure of the article to simulate how the fastener is mounted on the article. Similarly, if any other structural elements are built into the fastening system that alter the fastening system's resistance to peel mode disengagement, they should also be included in the sample preparation.
  (3) Attach a second leader to the second fastener portion. The leader should extend about 3 inches from the edge of the fastener and be about the same width as the widest portion of the fastening system. The leader should be an extension of the material on which the fastener is mounted on the product. If this is not possible, a suitable material should be chosen with similar modulus and bending stiffness as the material on which the fastener is mounted on the article. If the fastening system is not joined directly to the underlying structure of the article, as shown in FIGS. 6, 7, and 8 and described herein, the leader should be joined to the underlying structure of the article to simulate how the fastener is mounted on the article. Similarly, if any other structural elements are built into the fastening system that alter the fastening system's resistance to peel mode disengagement, they should also be included in the sample preparation.
  (4) Lay the first fastener portion on top of the second fastener portion such that their edges align as intended when fastened in a configuration for use of the product. Using the 11 pound roller, roll the combined first and second portions over the area including the fastening elements, rolling 4 times in the same direction without applying additional weight to the roller, at a velocity of 305 mm per minute (12 inches per minute). Note: An automated mechanical roller may be substituted for the hand-roller but must perform the above described rolling action.

Procedure

Figure 10:
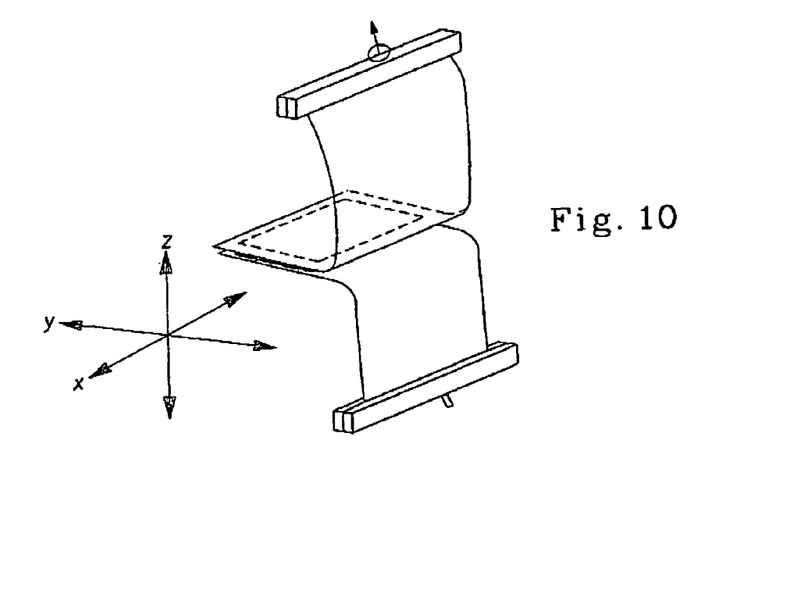
FIG. 10 is a perspective view of an exemplary fastening system of the present invention prepared for testing in accordance with the test method described herein.

The test procedure is performed according to the following steps:
  (1) Calibrate the instrument according the manufacturer's instruction.
  (2) Insert first leader into the bottom clamp such that about 0.75 inch of the leader (½ the gage length) is between the bottom clamp and the first edge of the connected sample, close the clamp.
  (3) Insert second leader into the top clamp such that about 0.75 inch of the leader (½ the gage length) is between the top clamp and the first edge of the connected sample with enough tension not to exceed 5 grams of force. The first edge of the connected sample should be about midway between the top and bottom clamps and ready to test. The sample should look as shown in FIG. 10 at this point.
  (4) Start the tensile tester, collect data throughout the peel.
  (5) When the specimen is completed return the crosshead to its original starting point (gage length).

Calculations

To calculate the Peak Load, read the load in Newtons from the curve/data. The Peak Load is the highest point on the curve/data for embodiments in which peel is intended to be uniform throughout the peel. For embodiments in which peel is not substantially uniform, for example as shown in FIGS. 4b, 4c, and 5, the sample may be evaluated in appropriate segments and the Peak Load within segments is reported.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. An article to be worn about a wearer comprising:
a surface fastening system having a primary direction of load bearing, the surface fastening system including a first surface fastening element and a second surface fastening element, the first fastening element being joined to the article, the second fastening element being disposed so as to be generally in a face to face relationship with the first fastening element when the surface fastening system is in an engaged configuration to fasten at least a portion of the article, wherein an unjoined portion of the second fastening element is unjoined from an underlying structure of the article, the unjoined portion including an unjoined dimension Y extending substantially parallel to a longitudinal axis of the article, the unjoined dimension Y increasing from a laterally outboard edge of the unjoined portion to a laterally inboard edge of the unjoined portion.

2. The article of claim 1, further comprising a chassis including an absorbent member.

3. The article of claim 1, wherein the article is selected from one of the group of an absorbent article, a diaper, a sanitary napkin, and a body wrap.

4. The article of claim 1, wherein the article is adapted to form a pant-like article.

5. The article of claim 1, wherein the unjoined portion includes a longitudinally inboard edge of the second fastening element.

6. The article of claim 1, wherein an overall shape of the unjoined portion is triangular.

7. The article of claim 1, wherein the second fastening element is joined to a carrier web and at least a portion of the carrier web is unjoined from the underlying structure of the article.

8. The article of claim 7, wherein at least a portion of the carrier web is extensible.

9. The article of claim 7, wherein at least a portion of the carrier web is elastomeric.

* * * * *